United States Patent [19]

Kaler et al.

[11] Patent Number: 4,956,065

[45] Date of Patent: Sep. 11, 1990

[54] METHOD AND APPARATUS FOR THREE DIMENSIONAL DYNAMIC DIELECTRIC LEVITATION

[76] Inventors: Karen V. I. S. Kaler, Dept. of Electrical Engineering, University of Calgary, 2500 University Drive, N. W., Calgary, Alberta, Canada, T2N 1N4; Thomas B. Jones, Dept. of Electrical Engineering, University of Rochester, Rochester, N.Y. 14627

[21] Appl. No.: 267,220

[22] Filed: Nov. 3, 1988

[51] Int. Cl.$^5$ ........................ C12M 1/42; C12N 13/00

[52] U.S. Cl. ............................ 204/183.1; 204/299 R; 204/180.1; 435/175; 435/287

[58] Field of Search ............ 204/183.1, 180.1, 299 R, 204/403; 435/291, 287, 173

[56] References Cited

PUBLICATIONS

Dynamic Dielectrophorectic Levitation of Living Individual Cells, Karan Kaler and Herbert A. Pohl, Transactions on Industry Applications, vol. 1A-19, No. 6 Nov./Dec. 1983.

Proceedings of the Second International Colloquium on Drops and Bubbles, JPL Publications 82-7, Dennis H. Le Croissette, Mar. 1, 1982.

Active Feedback-Controlled Dielectrophorectic Levitation, T. B. Jones and J. P. Kraybill, American Institute of Physics, J. Appl. Phys. 60(4), 15 Aug. 1986.

Bubble Dielectrophoresis, T. B. Jones and G. W. Bliss, American Institute of Physics, Journal of applied Physics, vol. 38, No. 4, Apr. 1977.

Dielectrophoretic Levitation of Spheres and Shells, T. B. Jones and G. A. Kallio, Journal of Electrostatics, 6(1979) 207-224, Elsevier Scientific Publishing Co., Amsterdam-Printed in the Netherlands.

*Primary Examiner*—John F. Niebling
*Assistant Examiner*—John S. Starsiak, Jr.
*Attorney, Agent, or Firm*—Burns, Doane, Swecker & Mathis

[57] ABSTRACT

A method and apparatus are disclosed which are directed to the use of dielectrophoresis to levitate, in three-dimensions, a neutral particle such as a biological cell. There is disclosed the use of dielectrophoresis wherein a unique combination of a particular electrode configuration and the use of an active feedback control system is utilized to obtain more precise dielectric properties of the particle.

8 Claims, 3 Drawing Sheets

METHOD AND APPARATUS FOR THREE DIMENSIONAL DYNAMIC DIELECTRIC LEVITATION

BACKGROUND OF THE INVENTION

The invention relates to the use of dielectrophoresis to levitate, in three-dimensions, a neutral particle such as a biological cell. More particularly, the invention relates to such a use of dielectrophoreses wherein a unique combination of a particular electrode configuration and an active feedback control is utilized to obtain more precise dielectric properties of the particle.

The need exists for methods of characterizing particles, particularly biological cells or their parts (e.g., organelles, ghosts, etc.). Such individual particles have unique characteristics and their identification and observation can be a powerful analysis tool to facilitate the study of the particles. In this regard, there is a particular need for a means to microscopically observe the characteristics of individual cells. That is, although different cells have different characteristics, when a number of cells are observed and analyzed simultaneously, there tends to be a masking of certain characteristics of the individual cells. The microscopic observation and analysis of a single cell would be particularly useful in the area of cancer diagnosis.

Non-uniform fields and in particular, dielectrophoretic methods have previously been used to separate and analyze biological cells. See e.g., U.S. Pat. Nos. 4,326,934 and 4,661,451, the contents of which are hereby incorporated by reference. Dielectrophoresis has been defined as the motion of a neutral particle due to the action of a non-uniform electric field on its permanent or induced dipole moment. When a particle is introduced into a system with a nonuniform electric field, the field induces a dipole in that particle. The divergent non-uniform nature of the field results in one end of the dipole being in a region of higher field strength than the other. The effect is that the dipole is pushed in the direction of the increasing field.

Non-uniform electric fields can induce translational and rotational motions of cells in suspension. The nonuniform field acts by aligning or inducing a dipole moment in the cell. The cell is then impelled by the field non-uniformity, usually towards the region of greatest field intensity.

The force created is known as the dielectrophoretic force, and the resulting motion dielectrophoresis. In the event the cell being acted upon is suspended in a polarizable medium, the net polarization of the whole may be such as to evoke a dielectrophoretic force in favor of pushing the body either into or away from the region of higher field intensity. The cell experiences "positive" dielectrophoresis when it is forced into the region of higher field intensity; "negative" dielectrophoresis results when the cell is pushed away from the region of higher field intensity.

It is well-known that a neutral particle, when subjected to the influence of a nonuniform, time varying (AC) electric field, may exhibit one of the following behaviors:

(1) Positive dielectrophoresis, i.e., attraction toward the region of high field intensity;

(2) Negative dielectrophoresis, i.e., repulsion toward the region of lower field intensity; or (3) Zeresis, i.e., no net displacement.

These processes arise from the following sequence of phenomena. The electric field induces a charge separation or dipole in the neutral particle. The resultant dipole consisting of equal numbers of slightly separated positive and negative charges now experiences a net force upon it because of the non-uniformity of the electric field. One or the other of the charge sets will be in a weaker electric field. Since the force upon a charge is exactly dependent upon the amount of charge, and upon the local field acting upon that charge, it will be seen that a net force arises upon the particle, despite the fact that it is neutral overall and has no excess charge of either type. The same considerations apply to the supporting fluid medium. The net of these dielectrophoretic forces upon the particle and its supporting medium acts to impel the particle toward the stronger field in positive dielectrophoresis. If, on the other hand, the net force upon the particle and medium is such as to impel the particle toward the region of weaker field, negative dielectrophoresis results.

In electrophoresis, the field induced motion of charged particles, the direction of the force is dependent upon the sign of the charge and upon the direction of the field. However, in dielectrophoresis, the force depends upon the square of the field intensity, and is independent of the direction of the field. For this reason, dielectrophoresis works well in AC fields. For a particle to experience either positive or negative dielectrophoresis it must be subject to a divergent electric field.

"Stable" levitation of a particle in a medium can be obtained with the use of a divergent electric field only if the time-average of the dielectrophoretic force at any point is constant, and if the thrust by the dielectrophoretic forces tend to push the particle into a region where the dielectrophoretic force is weaker. For example, if this dielectrophoretic force is to be balanced against gravity, then the field must weaken or diverge in the upward direction. Moreover, having the dielectrophoretic force on the particle lie in the direction away from the region of higher field intensity requires that negative dielectrophoresis be possible, i.e., that the effective time-average permittivity of the particle be less than that of the medium.

"Dynamic" levitation, on the other hand, means the suitable repetitive application of controlled positive dielectrophoresis such that essentially or nearly static localization of the particle is obtained. As an example, one could suspend a living cell in an aqueous medium below a pointed electrode by continually monitoring and adjusting the upward force to prevent the cell from falling away, yet not reaching and sticking to the upper electrode, nor touching the lower flat electrode.

Previously, there was developed a method for the dynamic dielectric levitation of living individual cells. See K. Kaler an H. Pohl, "Dynamic Dielectrophoretic Levitation of living Individual Cells", IEE Transactions on Industry Applications, Vol. 1A, 6, November/-December 1983, the contents of which is hereby incorporated by reference. That method was used to characterize individual cells. In the method, lone live cells were levitated by means of a dielectrophoretic force. This was done by observing the cell through a microscope and manually adjusting the voltage applied to the electrodes of the system to stabilize the cells in the electric field. The relative polarization of the cells and their aqueous support medium was then determined. When repeated over a range of frequencies, a spectrum of dielectric (polarization) responses was obtained which was used to characterize a single living cell. Unfortunately, although this method was a great advance in the art, it suffered from a variety of serious drawbacks. In particular, the manual nature of the method was inconvenient and imprecise. For example, for each run the spectrum of dielectric responses differed, thus adversely effecting the ability of the system to obtain reproducible results since different results were obtained every time. Also, it was difficult, if not impossible, to obtain suitably focussed cells because the cells were found to migrate radially in the field generated in that system.

SUMMARY AND OBJECTS OF THE INVENTION

Accordingly, it is a primary object of the invention to provide an improved method and apparatus for three-dimensional dynamic dielectrophoretic levitation and characterization.

It is a further object of the invention to provide for a method and apparatus for three-dimensional dynamic dielectrophoretic levitation and characterization in which the results which are obtained are more precise and which may be effectively reproduced.

It is even a further object of the invention to provide for a method and apparatus for three-dimensional dynamic dielectrophoretic levitation and characterization which can provide a suitably focussed particle and effectively prevent the radial migration of the particle.

Surprisingly, it has been discovered that the above objects of the invention can be obtained by the use of a unique combination of a particular electrode configuration and the use of an active feedback control. Generally, therefore, the invention it directed to a method and apparatus of three-dimensional dynamic dielectrophoretic levitation. The method comprises:

(i) providing a cell suspension in a levitation chamber of a dielectrophoresis apparatus containing an electrode system, the suspension being provided between the electrodes of the system;

(ii) subjecting a cell from the suspension to a nonuniform electric field generated from voltage applied to the electrodes of the electrode system, wherein there is established a non-uniform gradient that is positive along the axis extending between the electrodes and that is negative along the radial direction, thereby reducing radial migration of the cell;

(iii) dynamically levitating said cell in three-dimensions;

(iv) monitoring the position of the cell;

(v) providing a focussed cell by maintaining or adjusting the position of the cell by controlling the voltage applied to the electrode system, wherein steps (iv) and (v) are carried out using an active feedback control means.

In another aspect of the invention, a method for characterizing particles is provided wherein following the method for levitating particles outlined above, the polarization of the levitated particle is measured and then the method is repeated over a range of frequencies to characterize the particle.

In even another aspect of the invention an apparatus is provided to carry out the methods outlined above. The apparatus includes an active feedback control system and an electrode system which provides a nonuniform gradient that is positive along the axis extending between the electrodes of the system and negative along the radial direction.

Figure 1:
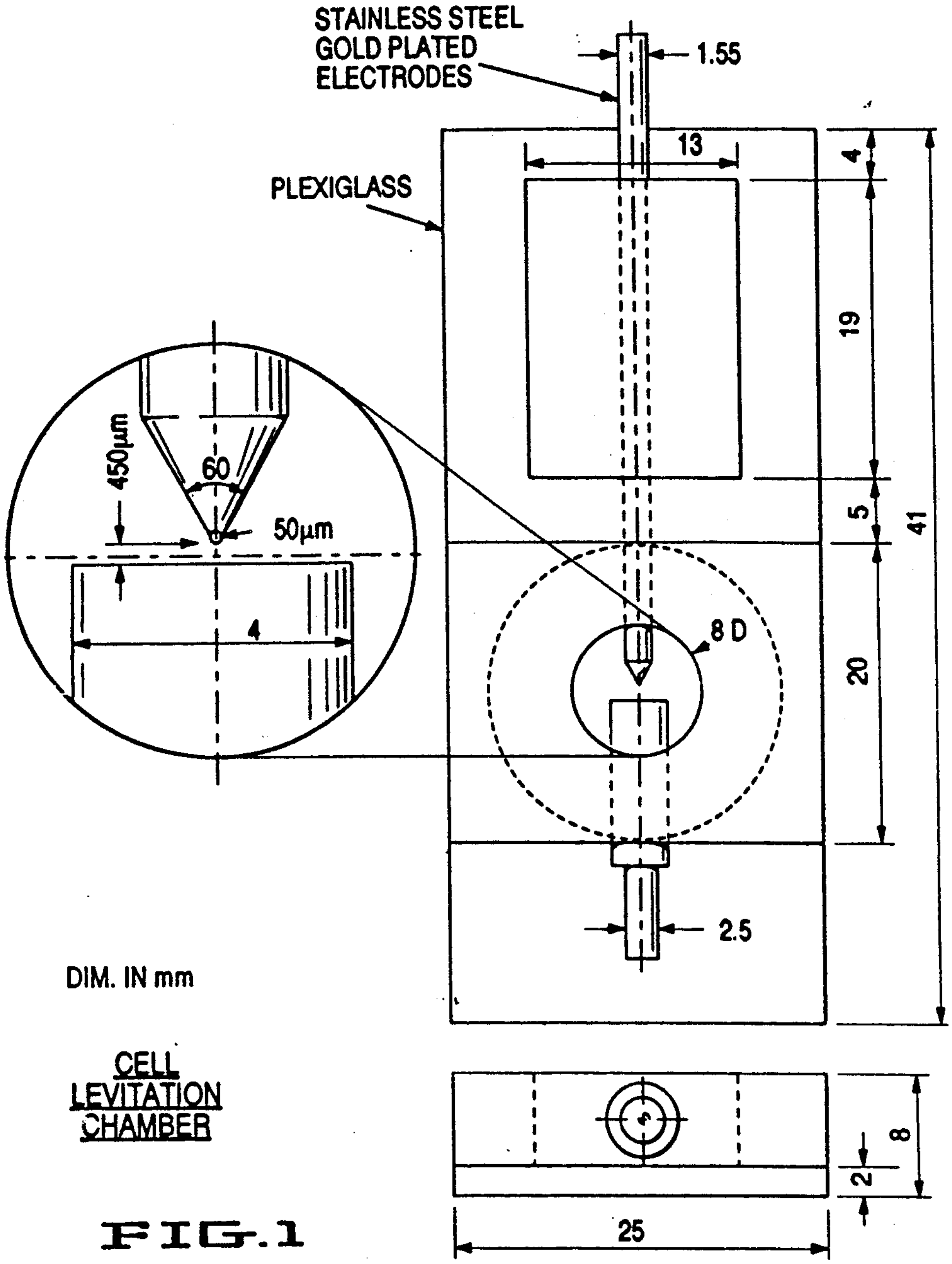
FIG. 1 is an illustration of a preferred electrode configuration and cell levitation chamber useful in the invention.

While the invention will be described in connection with a preferred embodiment thereof, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE PREFERRED EMBODIMENT

As noted above, the present invention is directed to the use of dielectrophoresis to characterize lone biological cells using a dynamic active feedback control levitation scheme. In this regard, an active levitation scheme is used as opposed to a passive one. The dielectrophoretic force acting on a spherical particle when placed in a non-uniform electric field is given by:

$$\vec{F}_{DEP} = 2\pi a^3\epsilon_o\epsilon_1 R_e\left\{\frac{(\epsilon_2^* - \epsilon_1^*)}{(\epsilon_2^* + 2\epsilon_1^*)}\right\}|\vec{\nabla}\vec{E}_o|^2 \quad (1)$$

or simply:

$$\vec{F}_{DEP}=2\pi\alpha^3\epsilon_0\epsilon_1\mathrm{Re}\{K_{eff}\}|\vec{\nabla}\vec{E}_0|^2 \quad (2)$$

where $\alpha$ is the particle radius with a complex dielectric permittivity $\epsilon_2^*$, $\epsilon_1^*$ is the complex medium permittivity, $\epsilon_0$ the permittivity of free space ($4\pi\times10^{-7}$ F/m), $E_0$ is the electrical strength, and $\epsilon_1^*=\epsilon_1-j\sigma_1/w$.

The above formulae show that the sign of $R_e(K_{eff})$, determines the direction of the dielectrophoretic force acting on the particle. In the case of bioparticles such as cells and organelles, it has been observed that $\epsilon_2^*$ is usually greater than $\epsilon_1^*$ over wide frequency ranges, the sign of the dielectrophoretic force is positive, i.e., directed toward the electric field intensity maxima. In such a case, the particle will experience a positive dielectrophorectic force and, therefore, to passively levitate such a particle requires an electric field maxima. Electric field maxima, however, can only exist at the electrode surfaces. Therefore, it is necessary to use dynamic levitation schemes involving active feedback control to achieve stable levitation.

With regard to conditions required for dynamic dielectrophoretic stabilization of a particle, for an axis symmetrical electrical field, with the particle in equilibrium located at a point $(O,z_o)$ on the axis, it has been shown that the voltage required to levitate the particle is given by:

$$2\alpha_0\alpha_1\mathrm{Re}\{K_{eff}\}V_0^2=m_g g \quad (3)$$

where $$m_g=4\pi(\gamma_2-\gamma_1)\alpha^2/3$$

If the particle is disturbed from this equilibrium point then it is necessary to use perturbations in the axial and radial directions to establish the conditions for stability. In this regard, dynamic or active feedback control levitation of particles is achievable so long as (i) $R_e(K_{eff})>0$ (ii) the electric field exhibits a negative radial gradient near the symmetry axis; and (iii) axial stabilization is achieved through some form of feedback control of the electrode.

The electrode system used in the present invention may vary. However, it is necessary that the electrode system be suitable to establish a non-uniform gradient that is positive along the axis extending between the electrodes and negative along the radial direction, thereby reducing radial migration of the cell. A preferred electrode system is the cone-plane electrode system illustrated in FIG. 1. It can be seen from FIG. 1 that the cone-plane electrode assembly includes a conic electrode and a grounded plane. The most preferred dimensions are also set forth in FIG. 1.

The electrode system may be housed in any suitable dielectrophoretic cell leviation chamber. A preferred such chamber is also illustrated in FIG. 1 which also includes the most preferred dimensions thereof. This chamber is a plexiglass chamber fitted with covered glass windows to aid in the optical monitoring of cell positions.

Figure 2:
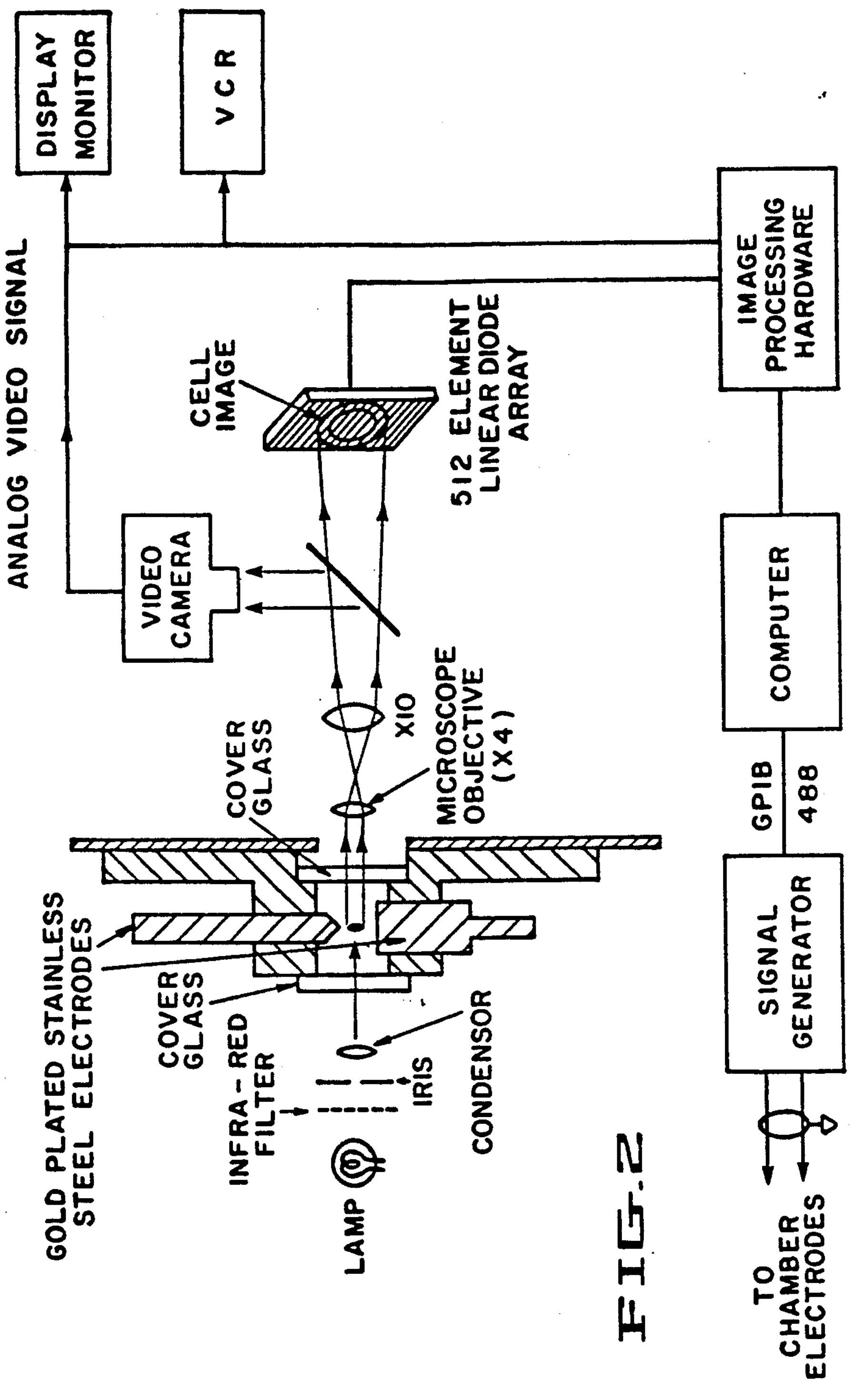
FIG. 2 is a diagram of a cell levitation apparatus useful in the present invention.

A preferred active feedback control means is illustrated in FIG. 2. The preferred optical system used to monitor the cell position includes a diode array and a video camera, which are used to detect cell position. The photodiode array is interfaced to a high speed A/D convertor (Data Precission), while the video camera is interfaced to real time image processing hardware (matrox). The video camera signal is fed to a display monitor and a video recorder.

Cell position may be determined using a threshold detection scheme. The threshold level is chosen so as to detect cell edges. This data can be made available to the levitation control software at a sampling rate (T) of 4 Hz. The control software for levitating the cell dynamically can be based on a simple linear proportional-integral (PI) control algorithm with the voltage required to levitate the particle given by:

$$V(nT) = e(nT)\,K_a + K_1 \sum_{k=1}^{k=n-1} \epsilon(kT)$$

where $K_e$, $K_i$ are the proportional and integral gain constants, k is the sample number, and e is the position error.

The following detailed Example is presented as a specific illustration of the presently claimed invention. It should be understood, however, that the invention is not limited to the specific details set forth in the Example.

Example

Figure 3:
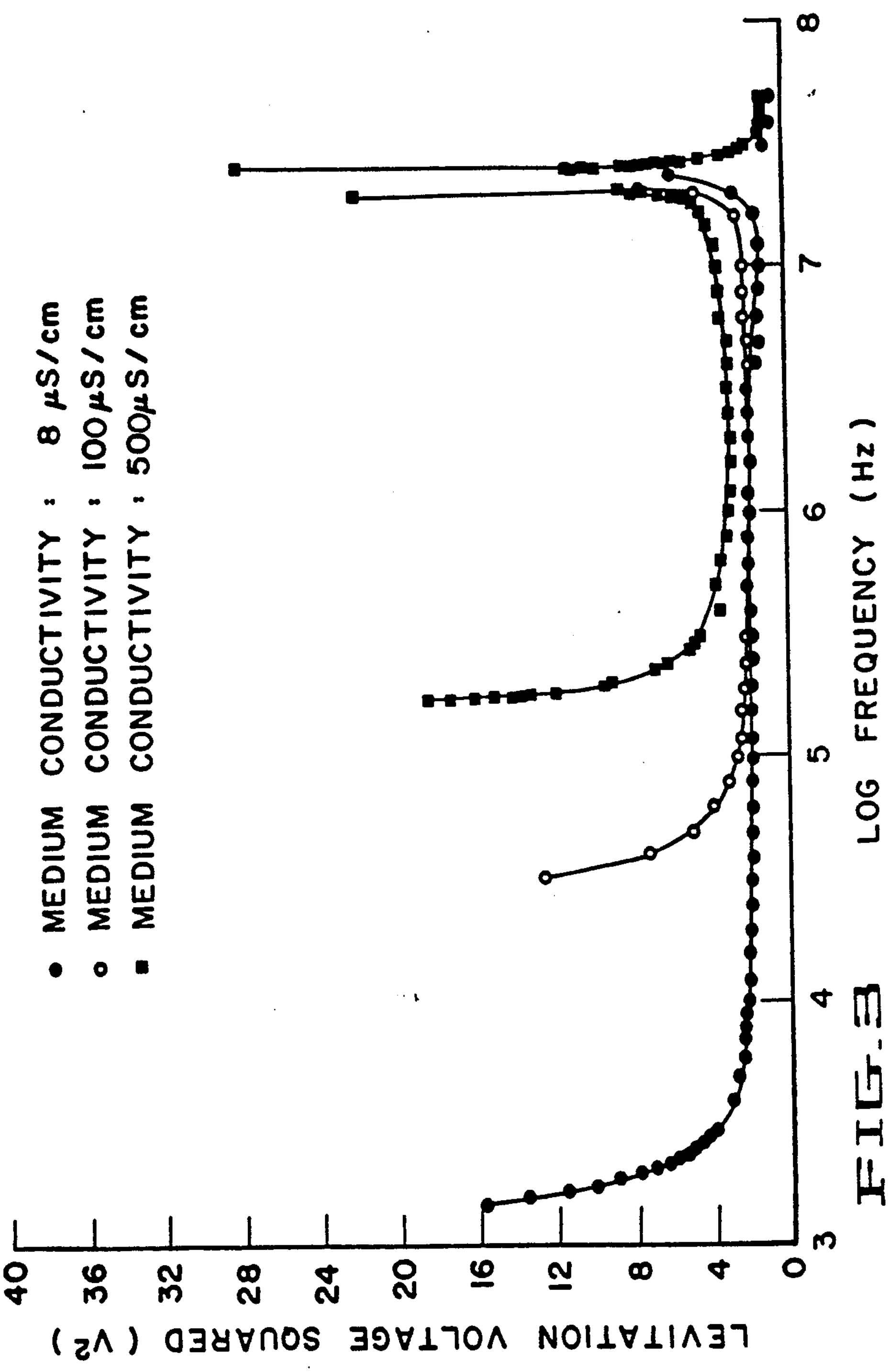
FIG. 3 is a graph illustrating the result of levitation voltage square versus frequency of the applied field for Canola protoplast suspended in an 8% Sorbitol solution.

Plant protoplast cells were harvested from Canola leaves and suspended in 8% Sorbitol solution of various conductivities made by adding KCl to the Sorbitol solution. The frequency dependent levitating spectrum for the same cells was obtained by levitation of the cells at a fixed position below the cone-tip electrode system illustrated in FIG. 1 using the cell levitation apparatus appearing in FIG. 2, while varying the frequency of applied voltage. FIG. 3 graphically illustrates the data obtained by varying the suspension conductivity on the levitation spectrum. In particular, FIG. 3 is a plot of the levitation voltage square versus frequency of the applied field for Canola protoplasts suspended in 8% Sorbitol solution.

The levitation spectra of Canola protoplasts exhibits three characteristic features. The lower frequency at which dynamic levitation can be achieved is highly sensitive to the medium conductivity. This frequency increases linearly with increasing conductivity of the external medium. Such polarization behavior has previously been produced and verified using the techniques of cellular spin resonance and dielectrophoresis. However, the low frequency responses may also be affected in a similar manner by the membrane conductivity and surface charge. Beyond the low frequency break point, the levitation spectrum is essentially flat before exhibiting another break point at around 22 MHz. Here the cell cannot be actively levitated due to negative dielectrophoresis. This break point is practically insensitive to the conductivity of the external medium and is considered to reflect the characteristic electrical properties of the cell membrane. At frequencies at and above 27 MHz, there is again a reversal of sign and hence levitation is again achievable. Polarization characteristics similar to this have previously been reported in studies where the rotation of the cell switched direction from counterclockwise to clockwise with respect to the applied rotating field.

The foregoing description of the invention in primary part portrays a particular preferred embodiment in accordance with the requirements of the patent statutes and for purposes of explanation and illustration. It will be apparent, however, to the those skilled in the art, that many modifications and changes in this specific apparatus and method may be made without departing from the scope and spirit of the invention. For example, other electrode configurations may be used so long as a nonuniform gradient that is positive along the axis extending between the electrodes and negative along the radial direction is obtained. Furthermore, other active feedback control devices may be used so long as the aforementioned purposes of the described means for feedback control are obtained. It is applicants' intention in the following claims to cover such modifications and variations as in the true spirit and scope of the invention.

What is claimed is:

1. A three-dimensional dynamic dielectrophoretic levitation method comprising:

(i) providing a cell suspension in a levitation chamber of a dielectrophoresis apparatus containing a electrode system, said suspension being provided between the electrodes of the system;

(ii) subjecting a cell from said suspension to a nonuniform electric field generated from voltage applied to the electrodes of said electrode system, wherein there is established a non-uniform gradient that is positive along the axis extending between the electrodes and negative in the radial direction, thereby reducing radial migration of the cell;

(iii) dynamically levitating said cell in three-dimensions;

(iv) monitoring the position of the cell; and (v) providing a focussed cell by maintaining or adjusting the position of the cell by controlling the voltage applied to the electrode system, wherein steps (iv) and (v) are carried out using an active feedback control means, said active feedback control means including an optical means to monitor cell position comprising both a linear diode array and a video camera wherein the diode array is interfaced with a high speed A/D converter and the video camera is interfaced with real time image processing hardware.

2. A three-dimensional dynamic dielectrophoretic levitation and characterization method comprising steps (i)-(v) of claim 1 and further comprising:

(vi) measuring the polarization of the cell; and (vii) repeating steps (i)-(vi) over a range of frequencies to characterize the cell.

3. A method according to claim 2, comprising generating the non-uniform electric field from voltage applied to the electrodes of a cone-plane electrode system.

4. A method according to claim 3, comprising generating the non-uniform electric field from voltage applied to the electrodes of a cone-plane electrode system, wherein $\theta$ of the conical electrode in the cone-plane electrode system is about 60° and the distance between the conical electrode and the plane electrode system is about 450 micrometers.

5. A three-dimensional dynamic dielectrophoretic levitation apparatus comprising:

(i) a levitation chamber containing an electrode system, wherein a cell suspension can be provided between electrodes of the system;

(ii) a voltage supply means to subject a cell from a cell suspension to a non-uniform electric field generated from the voltage applied to the electrodes of said electrode system, wherein a non-uniform gradient is established that is positive along the axis extending between the electrodes and negative in the radial direction to reduce radial migration of the cell; and (iii) an active feedback control means for monitoring the position of the cell and for providing a focussed cell by maintaining or adjusting the position of the cell by controlling the voltage applied to the electrode system, said active feedback control means including an optical means to monitor cell position comprising both a linear diode array and a video camera wherein the diode array is interfaced with a high speed A/D converter and the video camera is interfaced with real time image processing hardware.

6. A three-dimensional dynamic dielectrophoretic levitation apparatus according to claim 5 further comprising (iv) a means for measuring the polarization of the cell.

7. An apparatus according to claim 6, wherein the electrode system is a cone-plane electrode configuration.

8. An apparatus according to claim 7 wherein $\theta$ of the conical electrode in the cone plane electrode system is about 60° and the distance between the conical electrode and the plane electrode is about 450 micrometers.

* * * * *